US009303057B2

(12) United States Patent
Blanchard et al.

(10) Patent No.: US 9,303,057 B2
(45) Date of Patent: Apr. 5, 2016

(54) METHODS AND REAGENTS FOR ANALYZING RIBOSWITCHES USING FRET

(75) Inventors: Scott C. Blanchard, New York, NY (US); Ronald Micura, Innsbruck (AT); Andrea Haller, Innsbruck (AT)

(73) Assignees: CORNELL UNIVERSITY, Ithaca, NY (US); LEOPOLD-FRANZENS UNIVERSITAT INNSBRUCK, Innsbruck (AT)

( * ) Notice: Subject to any disclaimer, the term of this patent is extended or adjusted under 35 U.S.C. 154(b) by 517 days.

(21) Appl. No.: 13/459,989

(22) Filed: Apr. 30, 2012

(65) Prior Publication Data
US 2012/0276646 A1    Nov. 1, 2012

Related U.S. Application Data

(60) Provisional application No. 61/480,803, filed on Apr. 29, 2011.

(51) Int. Cl.
*C07H 21/04* (2006.01)
*C07H 21/02* (2006.01)
*C12N 15/115* (2010.01)
*G01N 21/64* (2006.01)

(52) U.S. Cl.
CPC ............. *C07H 21/02* (2013.01); *C12N 15/115* (2013.01); *C12N 2310/16* (2013.01); *C12N 2310/3519* (2013.01); *C12N 2320/50* (2013.01); *G01N 2021/6432* (2013.01); *Y10T 436/143333* (2015.01)

(58) Field of Classification Search
None
See application file for complete search history.

(56) References Cited

U.S. PATENT DOCUMENTS

2010/0286082 A1* 11/2010 Breaker et al. ............ 514/46

FOREIGN PATENT DOCUMENTS

WO    WO 2010/096720 A2    8/2010
WO    WO 2011/143575 A2    11/2011

OTHER PUBLICATIONS

Baird N.J. et al., "Idiosyncratically Tuned Switching Behavior of Riboswitch Aptamer Domains Revealed by Comparative Small-Angle X-Ray Scattering Analysis", *RNA* 16:598-609 (2010).
Blanchard S.C. et al., "tRNA Dynamics on the Ribosome During Translation", *PNAS* 101(35):12893-12898 (Aug. 31, 2004).
Blouin et al., "Riboswitches: Ancient and Promising Genetic Regulators", *ChemBioChem* 10:400-416 (2009).
Blanchard S.C. et al., "tRNA Selection and Kinetic Proofreading in Translation", *Nature Structural & Molecular Biology* 11(10):1008-1014 (Oct. 2004).
Brenner M.D. et al., "Multivector Fluorescence Analysis of the *Xpt* Guanine Riboswitch Aptamer Domain and the Conformational Role of Guanine", *Biochemistry* 49(8):1596-1605 (2010).
Corbino K.A. et al., "Evidence for a Second Class of S-Adenosylmethionine Riboswitches and Other Regulatory RNA Motifs in Alpha-Proteobacteria", *Genome Biology* 6(8):R70-R70.10 (2005).
Dave R. et al., "Mitigating Unwanted Photophysical Processes for Improved Single-Molecule Fluorescence Imaging", *Biophysical Journal* 96(6):2371-2381 (Mar. 2009).
Edwards A.L. et al., "Structural Basis for Recognition of S-Adenosylhomocysteine by Riboswitches", *RNA* 16(11):2144-2155 (2010).
Garst et al., "A Switch in Time: Detailing the Life of a Riboswitch" *Biochimica et Biophysica Acta* 1789:584-591 (2009).
Garst A.D. et al., "Riboswitches: Structures and Mechanisms", *Cold Spring Harbor Perspectives in Biology* pp. 1-13 (2010).
Gilbert S.D. et al., "Struture of the SAM-II Riboswitch Bound to S-Adenosylmethionine", *Nature Structural & Molecular Biology* 15(2):177-182 (Feb. 2008).
Haller A. et al., "Conformational Capture of the SAM-II Riboswitch", *Nature Chemical Biology* 7:393-400 (Jun. 2011).
Haller A. et al., "The Dynamic Nature of RNA as Key to Understanding Riboswitch Mechanisms", *Accounts of Chemical Research* 44(12):1339-1348 (2011).
Hammond M.C., "A Tale of Two Riboswitches", *Nature Chemical Biology* 7:342-343 (Jun. 2011).
Kelley J.M. et al., "Atomistic Basis for the On-Off Signaling Mechanism in SAM-II Riboswitch", *Nucleic Acids Research* 38(4):1392-1400 (2010).
Lemay J.-F. et al., "Folding of the Adenine Riboswitch", *Chemistry & Biology* 13:857-868 (Aug. 2006).
Stoddard C.D. et al., "Free State Conformational Sampling of the SAM-I Riboswitch Aptamer Domain", *Structure* 18:787-797 (Jul. 14, 2010).
Weigand J.E. et al., "Mechanistic Insights into an Engineered Riboswitch: A Switching Element Which Confers Riboswitch Activity", *Nucleic Acids Research* 39(8):3363-3372 (2011).

* cited by examiner

*Primary Examiner* — Kimberly Chong
(74) *Attorney, Agent, or Firm* — Scully, Scott, Murphy & Presser, P.C.

(57) ABSTRACT

The present invention is provides isolated riboswitches with FRET pairs for distinguishing changes in regulatory interactions controlled by the expression platform domain found in riboswitches. The invention further provides methods of using those riboswitches to detect structural changes in the expression platform domain and to identify potential antibiotics.

26 Claims, 9 Drawing Sheets

METHODS AND REAGENTS FOR ANALYZING RIBOSWITCHES USING FRET

CROSS-REFERENCE TO RELATED APPLICATIONS

This application claims priority from U.S. Provisional Application No. 61/480,803, filed Apr. 29, 2011, which is herein incorporated by reference in its entirety.

FIELD OF THE INVENTION

The present invention is provides isolated riboswitches with FRET pairs for distinguishing changes in regulatory interactions controlled by the expression platform domain found in riboswitches. The invention further provides methods of using those riboswitches to detect structural changes in the expression platform domain and to identify potential antibiotics.

BACKGROUND OF THE INVENTION

Riboswitches are non-coding messenger RNA (mRNA) elements that bind metabolites with high specificity to mediate gene expression control (Roth 2009). Riboswitches of numerous forms and functions, which recognize chemically diverse ligands with high selectivity, have been identified in bacteria, plants and fungi. The ubiquity of such mRNA regulatory elements highlights the need for a deeper understanding of their mechanism and mode of action.

As riboswitch domains are believed to regulate numerous essential genes in bacterial organisms, methods and reagents enabling direct insights into the riboswitch controlled transcription and translation regulation may have significant value in the discovery and/or tailoring of therapeutic agents specifically targeting one or more riboswitch domains.

Bacterial riboswitches generally operate through cis-acting control mechanisms, where a specific metabolite binds an aptamer domain in the mRNA's 5'-untranslated region in a manner that influences its propensity to adopt a specific fold (Roth 2009; Montange 2008). Structural investigations suggest that riboswitches respond to a metabolite's presence by adopting 'on' or 'off' conformations of the expression platform domain that up- or down-regulate the transcriptional or translational fate of the genes in which they are found (Blouin 2009). The capacity to influence transcriptional or translational expression in a ligand-dependent manner stipulates that a riboswitch adopts distinct ligand-free and ligand-bound conformations that exchange on a time scale that is timed with respect to the regulated event. The time scale of such dynamics and the nature of riboswitch conformational flexibility ensure a that the default regulatory pathway is favored in the absence of ligand. These events are also tuned to enable adequate time for metabolite recognition and for the conformational transition responsible for the regulatory outcome. A rapid response could be achieved if the riboswitch spontaneously and transiently adopts ligand-binding competent conformations. However, to avoid spurious signaling, such states must be unstable to ensure that the default folding pathway predominates in the absence of ligand.

Thus, methods and reagents that enable the direct assessment of riboswitch dynamics offer a unique means of assessing the regulatory switch underpinning riboswitch function and for evaluating responsiveness to specific metabolites and/or ligands.

Little is known about the nature of the apo-riboswitch conformation and how ligand-sensing transduces conformational changes in the expression platform to achieve alternative regulatory outcomes. (Garst 2009; Stoddard 2010; Baird 2010b; Edwards 2010)

To address these open questions, we present a detailed investigation of the ligand-induced folding process of the S-adenosylmethionine type II (SAM-II) riboswitch, as a model system for assessing riboswitch function since it possesses a compact fold, where both the aptamer domain and the expression platform domain (also referred to as the regulatory switch domain) are contiguous and defined by just 50 nucleotides. S-adenosylmethionine (SAM) is an important cofactor that represents the key methyl group donor for the methylation of various biomolecules. In bacteria, SAM is involved in methionine biosynthesis and related sulfur metabolic pathways. Its synthesis is frequently regulated via a riboswitch mechanism. Previous studies describe a total of five classes of SAM-binding riboswitches that each contains a binding pocket capable of discriminating among near-cognate derivatives, e.g., S-adenosylhomocysteine (SAH) (Wang 2008; Poiata 2009). The SAM-II riboswitch, occurring predominantly in proteobacteria, represent the class which is smallest in size (Corbino 2005). The crystal structure of a SAM-II riboswitch (from the 5'-UTR of the metX gene discovered in the Sargasso Sea metagenome) bound to SAM has been determined (Gilbert 2008). The findings revealed that the SAM-II riboswitch folds into a classical H-type pseudoknot (FIG. 1), where Loop L1 interacts with the major groove of the P2b helix in a triple helical arrangement. The Shine-Dalgarno (SD) sequence ( . . . AAAG$^{50}$G$^{51}$G$^{52}$-3'), a determinant of the expression platform domain of this riboswitch, lies within the 3'-purine-rich domain of the complex. This nucleoside stretch becomes masked by the riboswitch fold forming numerous hydrogen bonding contacts along the major groove of the P2b helix. The terminal residues of this region form stem P2a through two Watson-Crick base pairs with Loop L1 (G51: C15 and G50:C16).

In the course of the investigations leading to the present invention, the ligand-induced folding pathway of the SAM-II riboswitch was explored using a series of chemical and biophysical methods, including NMR, fluorescence spectroscopy and single-molecule fluorescence resonance energy transfer (smFRET) imaging (Haller 2011). The elucidated data indicated this riboswitch follows a multistep folding pathway that entails a dynamic conformational switching mechanism. Furthermore, the studies revealed that regional tertiary structure elements in the SAM-II riboswitch fold on distinct time scales, suggesting an ordered sequence of events in the ligand recognition process. These measurements shed light on the intrinsically dynamic nature of the SAM-II riboswitch, its propensity to exchange between distinct conformations and how these processes may impact the regulatory circuit of riboswitches in the regulatory control of gene expression.

Accordingly, the strategy, reagents and methods outlined in the present invention are directly applicable to other riboswitch domains of diverse types and functions. The direct implication from the model system employed is that riboswitch-mediated regulation hinges on metabolite and/or ligand-modulated dynamics, where ligand binding has a direct consequence on the mobility of the expression platform domain. Hence, the present invention addresses the need to follow structural changes of the expression platform domain under ligand binding and other conditions which was heretofore unavailable, and provides new reagents and methods for performing FRET analysis of the riboswitch.

SUMMARY OF THE INVENTION

Riboswitches are gene regulation elements in mRNA that function without the assistance of proteins by responding to the specific recognition of small-molecule ligands. While the ligand-bound states of riboswitches have proven amenable to structure determination efforts, structural features of riboswitches in their ligand-free forms and their ligand-response mechanisms giving rise to regulatory control have heretofore been lacking The present invention relates to isolated riboswitches or partial riboswitches which comprise an aptamer domain, an expression platform domain, and which have at least one fluorophore attached to the riboswitch. This fluorophore forms one partner of a FRET pair of fluorophores having FRET states capable of distinguishing changes in regulatory interactions controlled by said expression platform domain. In some embodiments the fluorophore is on the expression platform domain. In some embodiments, the regulatory interactions can be detected as structural changes in the expression domain in the presence and absence of a ligand for said riboswitch.

The riboswitches of the invention can further comprise a ribosome binding site. In some embodiments, the second fluorophore of the FRET pair is also attached to the riboswitch. In others, it is attached to the ligand for the given riboswitch, and in yet others, it is attached to a 30S subunit of a ribosome with the riboswitch can be bound to. The fluorophores of the FRET pair can be acceptor-donor fluorophores or donor-quencher fluorophores.

In some embodiments, the isolated riboswitch comprises a fluorophore on its expression platform domain which forms one partner of a FRET pair of fluorophores having FRET states capable of distinguishing changes in regulatory interactions controlled by the expression platform domain. For these riboswitches, the regulatory interactions can be detected as structural changes in the expression domain in the presence and absence of a ligand for the riboswitch. Likewise, these riboswitches can optionally have a ribosome binding site (e.g., a Shine-Dalgarno sequence with or without an AUG start codon). The fluorophores of the FRET pair can be acceptor-donor fluorophores or donor-quencher fluorophores.

In other embodiments, the isolated riboswitch comprises an aptamer domain, an expression platform domain, and a FRET pair of fluorophores which have FRET states capable of distinguishing changes in regulatory interactions controlled by said expression platform domain. For these riboswitches, the regulatory interactions can be detected as structural changes in the expression domain in the presence and absence of a ligand for the riboswitch. Likewise, these riboswitches can optionally have a ribosome binding site (e.g., a Shine-Dalgarno sequence with or without an AUG start codon). In some cases, one fluorophore of the pair is on the expression platform domain and the other fluorophore of the pair is on the aptamer domain. The fluorophores of the FRET pair can be acceptor-donor fluorophores or donor-quencher fluorophores.

Examples of riboswitches of the invention include, but are not limited to, an adenine riboswitch, a guanine riboswitch, a 2'-deoxyguanosine riboswitch, a preQ1 I-II riboswitch, a SAM I-IV riboswitch, a SAH riboswitch, a cobalamin B12 riboswitch, a fluorine riboswitch, an FMN riboswitch, a TPP riboswitch, a lysine riboswitch, a glycine riboswitch, a THF riboswitch, a glutamine riboswitch, a glmS riboswitch, a molybdenum cofactor (MoCo) riboswitch, or a cyclic di-GMP riboswitch.

In a preferred embodiment the riboswitch of is S-adenosylmethionine (SAM) type riboswitch, and even more preferably a SAM-type II riboswitch. On site of labeling for SAM-II type riboswitch is at nucleoside positions 14 and 52; another site is at nucleosides 16 and 50.

Any of the riboswitches of the invention can further comprise an immobilization moiety, to enable surface immobilization or immobilization to a solid support. Conveniently, the immobilization moiety can be at the 5' end of the riboswitch. In any event, it is positioned so that it does not interfere with movement of the expression platform domain in the context of its regulatory interactions.

Another aspect of the instant invention provides methods to detect structural changes in the expression platform domain of a riboswitch by determining the FRET states of a riboswitch of the invention for a time and under varying conditions. Conditions which can be varied, include but are not limited to, the presence or absence of a ligand for the riboswitch, changing concentrations of the ligand, the presence or absence of a cofactor that interacts with the riboswitch, changing concentrations of the cofactor, presence or absence of transcription components, changing concentrations of the transcription components, presence or absence of translation initiation components, and changing concentration of the translation components.

This methods can further comprise the step of adding a modulator of riboswitch activity to the reaction and determining the FRET states of the a riboswitch in the presence of the modulator. As discussed herein, changes in FRET states indicate the relationship between aptamer domain binding and sequestration or liberation of the expression platform domain. FRET states are detected by bulk fluorescence detection or by smFRET imaging techniques.

Yet another aspect of the invention is directed to methods to identify a compound that interferes with riboswitch function. In accordance with this method, a riboswitch of the invention is surface-immobilized, a test compound is added and changes in FRET states are monitored or detected using smFRET imaging techniques to assess how the test compound modulates or alters the FRET states and the dynamic exchange between the FRET states. In these methods, a FRET pair is present and sensitive to transitioning between low FRET states and high FRET states under transcription and/or translation competent conditions and the test compound's effects are monitored or detected as changes in FRET states using smFRET imaging techniques to identify a test compound capable of (i) stabilizing said riboswitch in a low FRET state, an intermediate FRET state or in a high FRET state, (ii) changing said riboswitch's distribution among low, intermediate and high FRET states, (iii) changing the riboswitch's rate of transition among low, intermediate and high FRET states, or (iv) abolishing FRET. A test compound is identified as a candidate antibiotic when the test compound causes the riboswitch to adopt a FRET state which correlates with cytotoxicity to bacteria.

LC-ESI mass spectrum of purified ligation product. (d) Fluorescence emission response of the acceptor dye in the Cy5/Cy3 labeled SAM-II construct upon consecutive $Mg^{2+}$ and SAM addition under conditions where $c_{RNA}$=0.5 μM, $c_{SAM}$=5.0 μM, $c_{mg}$=2.0 mM, 50 mM KMOPS, 100 mM KCl, 20° C., pH 7.5; $\lambda_{ex}$=540 nm, $\lambda_{em}$=665 nm.

Figure 3:
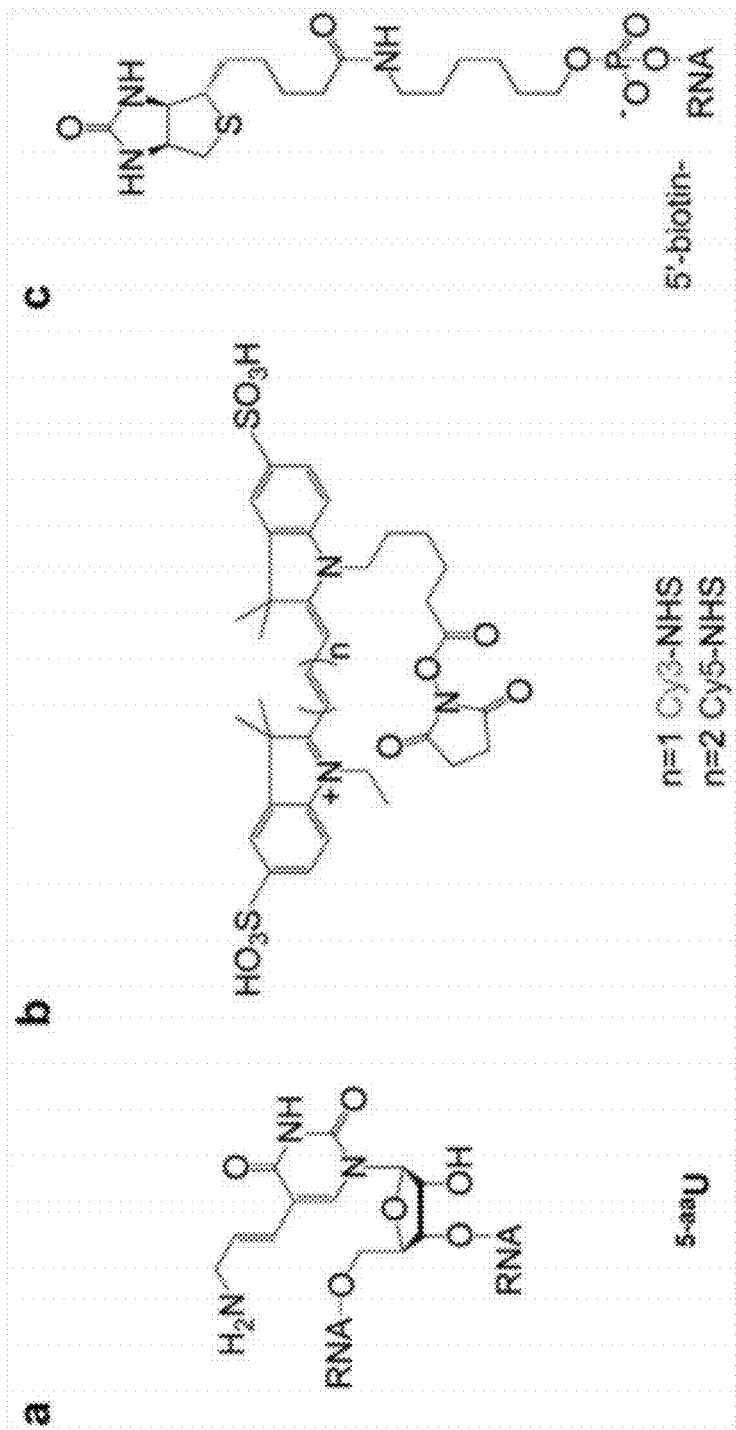

FIG. 3 provides the chemical structures of (a) 5-aminoallyluridine in RNA ($^{5-aa}$U); (b) N-hydroxysuccinimide esters of the cyanine dyes Cy3 and Cy5 attached to $^{5-aa}$U-labeled RNA fragments; and (c) biotin and linker moiety at the 5'-end of the RNA for smFRET experiments.

Figure 4:
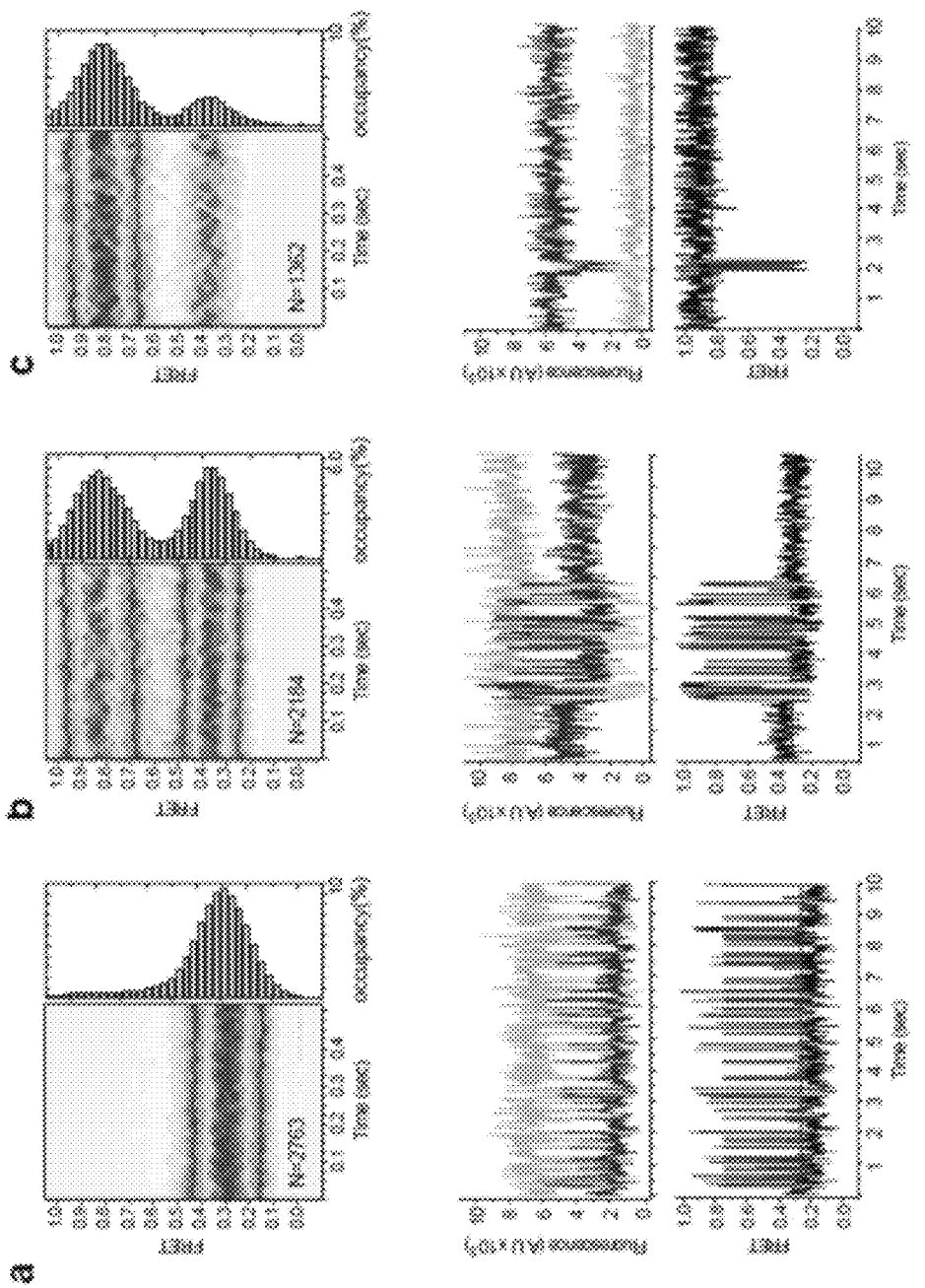

FIG. 4 illustrates the dynamics of pseudoknot formation of the SAM-II riboswitch analyzed by smFRET experiments. (a) Upper panel: population FRET histograms showing the mean FRET values and percent (%) occupancies of each state observed for the SAM-II riboswitch in the absence of $Mg^{2+}$ and SAM ligand. Lower panels: Fluorescence (light-Cy3; dark-Cy5) and FRET (blue or dark) trajectories of individual SAM-II riboswitch molecules under the same conditions, where idealization of the data to a two-state Markov chain is shown in red (or light). (b) Same as (a) but in the presence of 2 mM $Mg^{2+}$ ions. (c) Same as (a) but in the presence of 2 mM $Mg^{2+}$ ions and 10 μM SAM.

Figure 5:
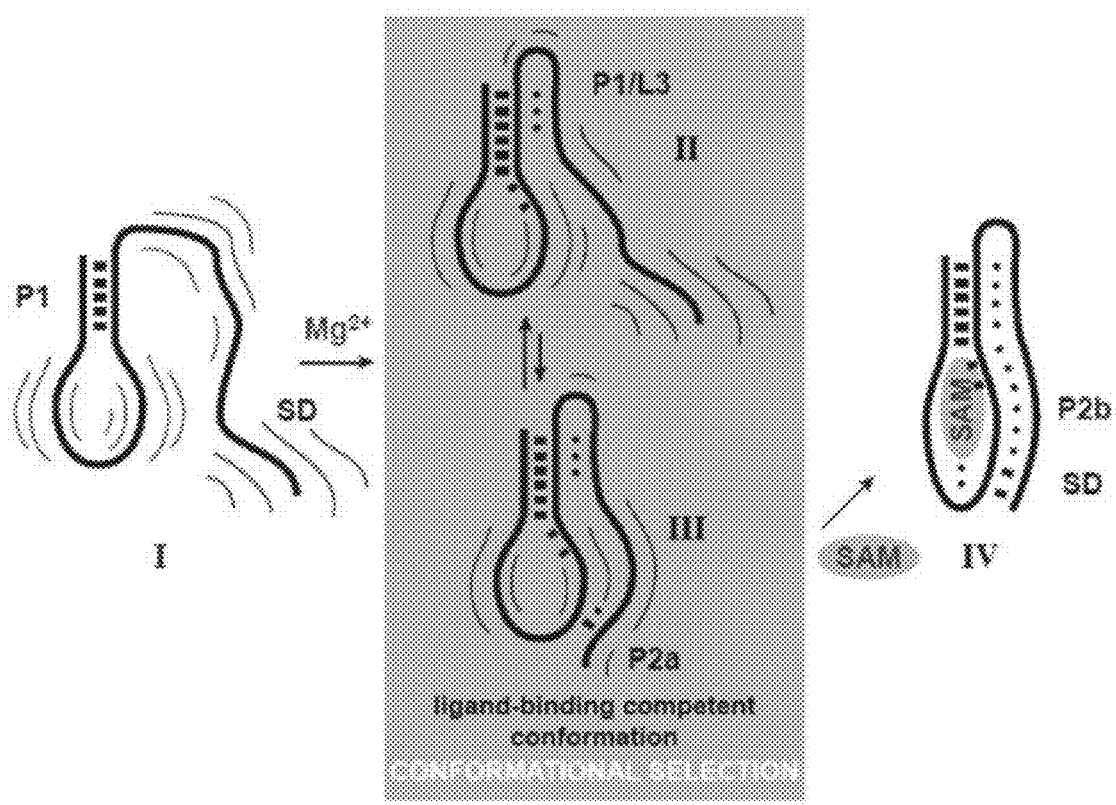

FIG. 5 depicts a folding model of the SAM-II riboswitch. The experimental data support a model where $Mg^{2+}$ ions stabilize the P1/L3 segment of the riboswitch to a significant extent, thereby also supporting the preorganization of loop L1 together with the binding pocket (II). Moreover, in the presence of $Mg^{2+}$, the transient pseudoknot-like folds in the ensemble III reach 10-fold increased lifetimes (subsecond regime). SAM selects (or "captures") fold III and adaptive, conformational rearrangements occur in distinct order, even in distal regions to the binding site. The culmination of the process is formation of stem P2a which masks the Shine-Dalgarno (SD) sequence (IV) and thereby renders recognition by the ribosome unfeasible, hampering translation initiation.

Figure 6:
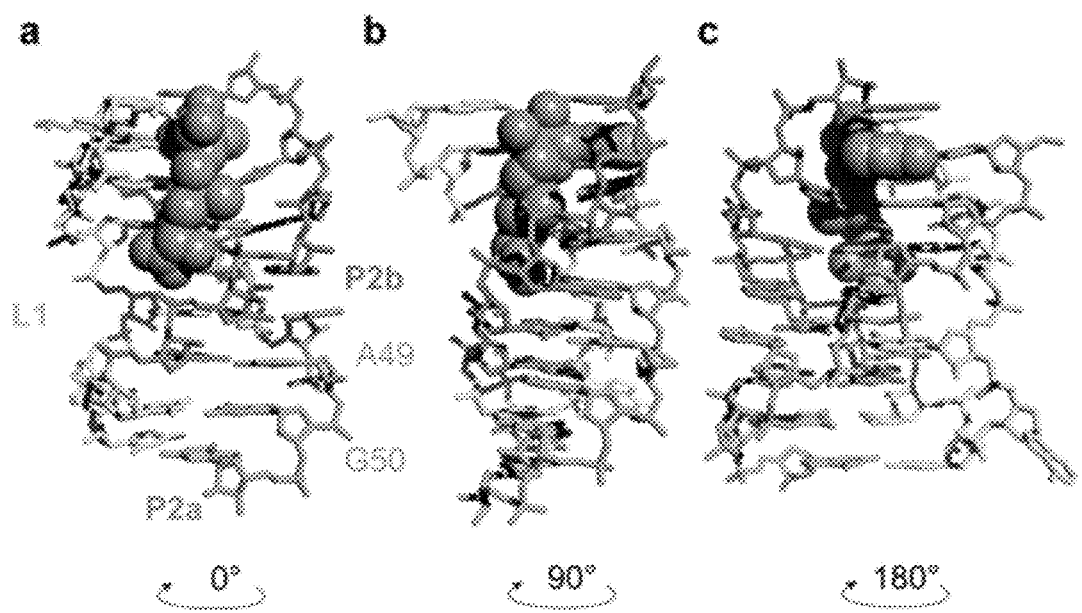

FIG. 6 illustrates SAM access to the binding pocket of the SAM-II riboswitch, in different views on the P2b/L1/P2a region (a-c). Coordinates provided according to PDB 2QWY (Gilbert 2008).

Figure 7:
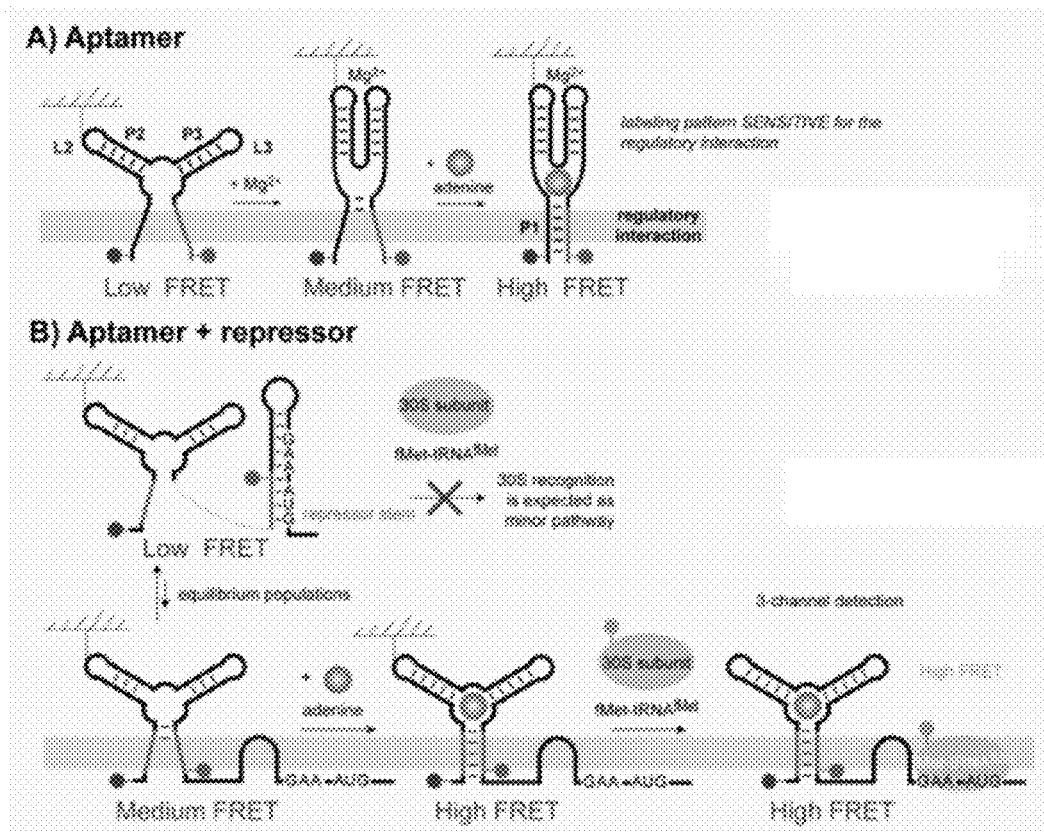

FIG. 7 shows labeling patterns and expected signals (low, medium, high FRET) for smFRET experiments with the add A-riboswitch aptamer domain (A) and a full-length riboswitch with aptamer and expression platform domains (encompassing the repressor stem). Various ribosomal components are shown.

Figure 8:
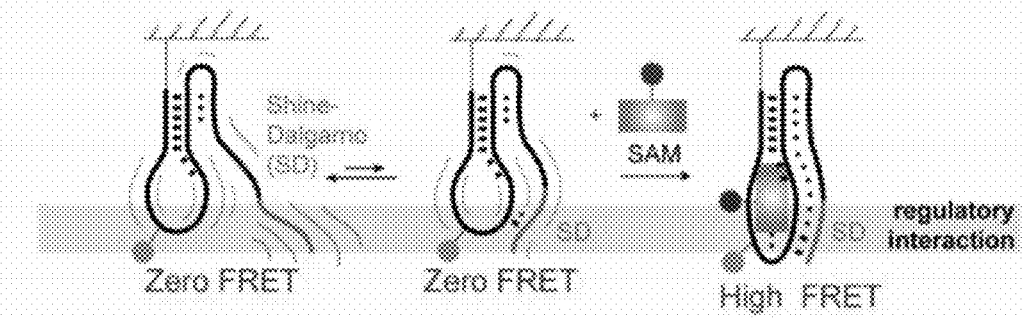
Figure 8:
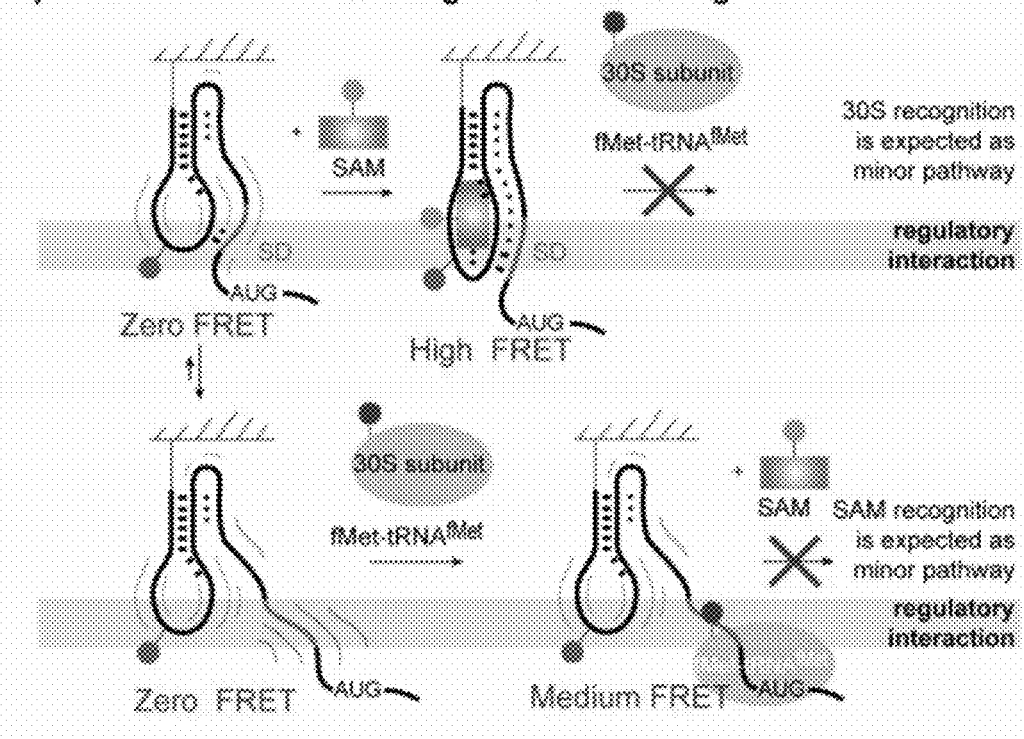

FIG. 8 shows various smFRET experiments using Cy-labeled SAM derivatives and the SAM-II riboswitch class.

Figure 9:
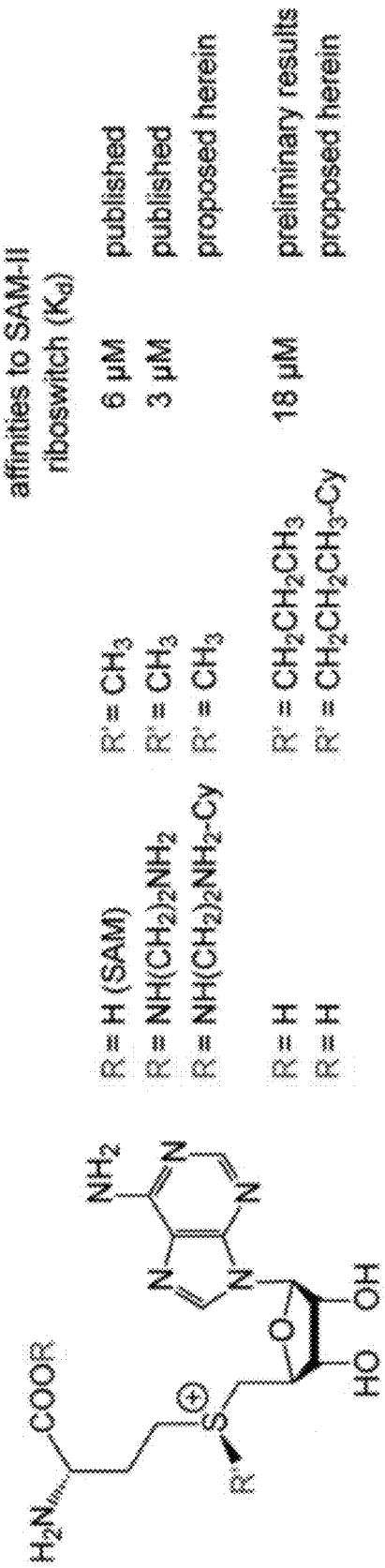

FIG. 9 depicts modified SAM ligands having high affinities for the SAM-II riboswitch.

DETAILED DESCRIPTION OF THE INVENTION

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

1. Definitions

"Single-molecule fluorescence resonance energy transfer" (or "smFRET") is the application of FRET techniques to study a single molecule with at least two fluorescent labels (or a fluorophore and quencher as described below), or the interaction of at least two molecules, each with a label. Fluorescence Resonance Energy Transfer (FRET) is a non-radiative pathway by which a molecule in an electronic excited state may relax back to the more stable ground state. The transfer of energy occurs through space via dipole-dipole interaction: energy from the excited state molecule (the donor fluorophore) may transfer to a neighboring molecule (the acceptor fluorophore) given significant degree of spectral overlap between donor emission and acceptor absorption, properly oriented dipole moments of the interacting dye molecules, and the appropriate distance between the two fluorophores. The Förster relationship defining the efficiency of FRET as a function of distance is unique for each dye pair. In smFRET the donor and receptor fluorophores are on the same molecule, or are on different molecules that interact, bringing the two fluorophores into proximity. The detection of FRET at the single-molecule scale enables the direct measurement of conformational events and/or binding processes on biologically-relevant time scales. Methods to perform smFRET imaging are known in the art, and are described, for example, in Blanchard 2004. Methods to attach translationally competent ribosomes to a surface are described, for example, in U.S. Pat. No. 7,297,532. such techniques are generally applicable to other biomolecules, including riboswitches.

Dynamic smFRET refers to the use of smFRET techniques to interrogate biological samples of interest over extended periods of time in order to quantify changes in the amount of time that the sample spends in its various conformational states. By measuring time-dependent conformational dynamics in a biomolecule, insights into the physical parameters of motion are obtained that relate to regulation and function. These techniques also enable the skilled artisan to compute FRET state distributions.

The labels used herein will generally comprise fluorophores. A "fluorophore" is a component of a molecule which causes a molecule to be fluorescent. It is a functional group in a molecule which will absorb energy of a specific wavelength and re-emit energy at a specific wavelength. The amount and wavelength of the emitted energy depend on both the fluorophore and the chemical environment of the fluorophore. Fluorescein isothiocyanate (FITC), a reactive derivative of fluorescein, has been one of the most common fluorophores chemically attached to other, non-fluorescent molecules to create new fluorescent molecules for a variety of applications. Other common fluorophores are derivatives of rhodamine (TRITC), coumarin, and cyanine Newer generations of fluorophores such as the CF dyes, Cyanin (Cy) dyes, the FluoProbes dyes, the DyLight Fluors, the Oyester dyes, the Atto dyes, the HiLyte Fluors, and the Alexa Fluors are claimed to be perform better (more photostable, brighter, and/or less pH-sensitive) than other standard dyes of comparable excitation and emission. Fluorophores especially useful for practicing the instant invention are described in PCT application PCT/US10/24824.

The fluorophore may incorporate or be located proximally to a "protective agent" (or "quencher" or "triplet state quencher" or "fluorescence modifier", in particular embodiments), which is a molecule or a moiety (i.e., chemical group) that has the ability to alter the photophysical properties of a fluorophore, particularly by altering the light state-dark state (i.e., singlet-triplet) occupancy distribution or relaxation pathway of excited and relaxing electrons. The ability of a molecule to function as a protective agent is often evidenced by its ability to alter the blinking and/or photobleaching characteristics of a fluorophore.

Those of skill in the art can readily select appropriate donor-acceptor or donor-quencher pairs for FRET in accordance with the invention as well as modify riboswitches or other biomolecules of the invention to attach the donor and acceptor fluorophores in site-specific manner without substantially altering functionality of the riboswitch or biomolecule.

The FRET states described herein depend upon the selected FRET pair used to interrogate structural transitions. FIG. 4 shows an example of low FRET and high FRET states using a Cy3/Cy5 FRET pair on a SAM-II riboswitch.

Riboswitches are 5' regulatory elements found in the non-coding region of mRNA upstream of the start codon. Riboswitches have two domains, an aptamer domain and an expression platform domain. The aptamer and expression platform domains are typically in dynamic exchange between unfolded states and multiple, transient conformations in the absence of ligand. The term riboswitch as used herein can mean a complete or partial riboswitch.

The aptamer domain is the sequence required for ligand binding with high specificity and high selectivity. For most riboswitches, the aptamer domain is on the 5' side of the complete riboswitch sequence. The aptamers show robust binding affinities for their dedicated ligands, which frequently are metabolites and allows the riboswitch to participate in regulating biosynthesis and/or transport of the metabolite.

The expression platform domain (sometimes referred to the regulatory domain) is generally immediately downstream (3') of the aptamer domain, an may overlap the aptamer domain. For riboswitches that regulate protein synthesis, the expression platform domain can include the Shine-Dalgarno sequence and/or the translational start codon. For riboswitches that regulate transcription, the expression platform participates in adopting and switching between anti-terminator and terminator structures which are the structural elements responsible for RNA polymerase read-through and continued synthesis or for aborting RNA synthesis, respectively. Ligand binding determines which structure is formed and hence the regulatory response. Thus, the structure assumed by the expression platform domain determines the on or off signal of gene expression to the transcriptional, translational or splicing machinery.

When the expression platform domain partially overlaps with the aptamer domain, it creates a physical link between the two domains such that folding patterns of the aptamer and expression platform domains can be mutually exclusive.

2. Riboswitches for Expression Platform Domain Investigations smFRET investigations with riboswitches have been reported only in context of following changes in the aptamer domain (Lemay 2006; Brenner 2010). In these constructs, the regulatory helix (expression platform domain) was used as an anchor for immobilization. The labeling patterns used in those studies were specifically designed appropriate to probe the dynamics of the aptamer domain and did not investigate the dynamics of the expression platform domain.

However, such studies were inadequate to reveal dynamics of the expression platform domain or to investigate riboswitch-modulated gene expression. The present invention, by selection of the FRET pairs as described herein, overcomes this limitation in the art and provides methods to modulate riboswitch regulatory activity and to explore ligand-induced riboswitch-mediated control of gene expression.

Accordingly, the present invention is directed to riboswitches having at least one fluorophore attached to its expression platform domain or to riboswitches which are capable, when paired with another fluorophore, of interrogating the structural variations and/or regulatory interactions of the expression platform domain. In one embodiment, a riboswitch of the invention comprises an aptamer domain, an expression platform domain, and at least one fluorophore attached to the riboswitch and which fluorophore can form one partner of a FRET pair of fluorophores having FRET states capable of distinguishing changes in regulatory interactions controlled by said expression platform domain. In another embodiment, a riboswitch of the invention comprises an aptamer domain, an expression platform domain, and at least one fluorophore attached to the riboswitch and which fluorophore can form one partner of a FRET pair of fluorophores having FRET states capable of distinguishing structural changes in the expression platform domain in the presence and absence of a ligand for that riboswitch. For example, such riboswitches are useful for finding compounds that inhibit or activate riboswitch regulatory activity, allowing identification of potential new antibiotics or therapeutic agents.

More generally, every riboswitch provides a structural interaction (at the secondary or tertiary structure level) that is responsible for directing the folding pathway into one or the other mutually exclusive structures responsible for preventing or enabling gene expression. Such structural interactions occur with the expression platform domain and are called the "regulatory interaction." The dynamics of this interaction can be revealed by smFRET to provide important insights into the molecular mechanism and general response mode of a riboswitch by positioning labels to monitor changes in the expression platform domain and thereby interrogate the regulatory structural element(s). Hence, the observation of dynamics using smFRET (or bulk fluorescence) enables one to follow the opening and the closing of the expression platform domain if the two labels are proximal to each other in the closed structure and distal from each other in the open structure. In one embodiment, a fluorophore is positioned in the expression platform domain and the other fluorophore is in the aptamer domain.

Labels (fluorophores), such as those described in the definition section, can be attached by methods known in the art. For example and without limitation, the skilled artisan can use biotin, click chemistry, active esters chemistry, or Staudinger ligation and the like.

For translationally-controlled riboswitches, for example, one label can be attached at the SD sequence and the other label can be found within the RNA sequences that sequester the SD sequence in the "off" state (generally within the aptamer).

For transcriptionally-controlled riboswitches, for example, one label can be positioned in the sequence stretch that alternates between being sequestered in the terminator stem-loop and being accessible in the antiterminator structure while the other label can be positioned as close as possible (through space) to the first label when the terminator stem-loop is fully formed.

For riboswitches that form pseudoknots (including but not limited to SAM-II, SAM-V, preQ1-I, and preQ1-II), one label can be be placed in the 5' loop element of the aptamer domain and the other label in the 3'-single-stranded region neighboring the Shine-Dalgarno sequence and/or AUG start codon, which comes into close proximity with the aptamer domain upon ligand binding. An ideal labeling strategy is one in which the base to which the fluorophore is linked forms the closing base pairs of the pseudoknot conformation that is stabilized by the ligand.

For riboswitches that form 3-way and 4-way junctions such as the SAM-I, SAM-IV, adenine, guanine, FMN, TPP (thiamin pyrophosphate), SAH, and cyclic-diGMP (cyGG) riboswitches, the regulatory interaction is usually represented by stem P1. Accordingly, the two labels are put on the opposite strands forming the double helix of P1.

As described above, labels are located at appropriate locations on the riboswitch. To select suitable positions to introduce fluorophores, the three-dimensional structure of a riboswitch can be analyzed following the criteria of retaining hydrogen-bonding patterns and of maintaining highly conserved sequence portions. By doing this, about 10 to 15% of sites within the sequence can be identified that participate in secondary and tertiary structural interactions and that fulfill the above mentioned criteria. If the crystal structure is not available, SHAPE analysis can provide a helpful tool since nucleosides that become more flexible in the metabolite-bound RNA usually correspond with nucleosides that are looped out or at least partially unstacked (Gilbert 2008; Lu 2010).

Other methods to identify sites appropriate for riboswitch labeling include structure prediction algorithms (e.g., MFold), bulk experiments using environment-sensitive fluorophore probes (e.g., 2-aminopurine) as well as chemical and/or enzymatic probing techniques (e.g., dimethysulfate modification of the RNA bases or RNAse protection assays, respectively).

Examples of riboswitches useful in the present invention include, but are not limited to, those listed in the following paragraphs. Additionally, the labeling sites for FRET pairs is also illustrative and should not be construed as limiting. Hence, homologous riboswitches can have similar (even identical) labeling sites. By way of example, a TPP riboswitch from a different species of bacteria (such as a *Salmonella* spp.) can also have one label at or between nucleosides 9-14 and the second label at or between nucleosides 86-91. In this regard the exact location of the labeling site can vary a few nucleotides, typically 1-3, based on slight sequence differences that may be present among homologous riboswitches. One of skill in the art can compare homologous riboswitches to those illustrated herein or otherwise known in the art, to identify the analogous labeling sites, aptamer domains (AP) and expression platform domains (EP).

For the TPP riboswitch, one label can be at or between nucleosides 9-14 and the other label is at or between nucleosides 86-91. Alternatively, one label can be at or between nucleosides 65-75 and the other is at or between nucleosides 25-35. This numbering system is from the *E. coli* thiM TPP riboswitch with an AP at nucleosides 1-85 and an EP at nucleosides 70-100.

For the preQ1 class I riboswitch, one label can be at or between nucleosides 7-10 and the other is at or between nucleosides 30-37. Alternatively, one label can be at or between nucleosides 18-22 and the other is at or between nucleosides 30-37. This numbering system is from *F. nucleatum* preQ1 class I riboswitch with an AP at nucleosides 1-34 and an EP at nucleosides 30-70.

For the preqQ1 class II riboswitch, one label can be at or between nucleosides 8-14 and the other label is at or between nucleosides 50-62. Alternatively, one label can be at or between nucleosides 8-14 and the other label is at or between nucleosides 39-45. This numbering system is from *Streptococcus pneumoniae* preQ1 class II riboswitch with an AP at nucleosides 1-55 and an EP at nucleosides 50-80.

For the purine and 2'-deoxyguanosine riboswitch, one label can be at or between nucleosides 9-20 and the other label is at or between nucleosides 50-62. Alternatively, one label can be at or between nucleosides 8-14 and the other label is at or between nucleosides 76-90. This numbering system is from the add adenine riboswitch with an AP at nucleosides 1-75 and an EP at nucleosides 55-140.

For the SAH riboswitch, one label can be at or between nucleosides 45-55 and the other label is at or between nucleosides 14-19. Alternatively, one label can be at or between nucleosides 45-55 and the other label is at or between nucleosides 1-5. Another alternative is to have one label at or between nucleosides 45-55 and the other label at or between nucleosides 20-25. This numbering system is from the *Ralstonia solanacearum* SAH riboswitch with an AP at nucleosides 1-45 and an EP at nucleosides 40-100.

For the fluorine riboswitch, one label can be at or between nucleosides 1-5 and the other label is at or between nucleosides 14-23. Alternatively, one label can be at or between nucleosides 1-5 and the other label is at or between nucleosides 28-33. Another alternative is to have one label at or between nucleosides 48-55 and the other label at or between nucleosides 1-33. This numbering system is from the *Thermotoga petrophila* fluorine riboswitchwith an AP at nucleosides 1-40 and an EP at nucleosides 35-100.

For the FMN riboswitch, one label can be at or between nucleosides 1-10 and the other label is at or between nucleosides 100-112. Alternatively, one label can be at or between nucleosides 15-25 and the other label at or between nucleosides 85-95. A further alternative is to have one label at or between nucleosides 35-45 and the other label at or between nucleosides 100-115. This numbering system is from the *Fusobacterium nucleatum* FMN riboswitch with an AP at nucleosides 1-110 and an EP at nucleosides 90-280.

For the lysine riboswitch, one label can be at or between nucleosides 1-10 and the other label at or between nucleosides 165-175; or one label can be at or between nucleosides 145-155 and the other label at or between nucleosides 165-175; or one label can be at or between nucleosides 120-135 and the other label at or between nucleosides 165-175. This numbering system is from the *Thermotoga maritima* lysine riboswitch with an AP at nucleosides 1-175 and an EP at nucleosides 150-220.

For the glycine riboswitch, one label can be at or between nucleosides 1-8 and the other label at or between nucleosides 80-90; or one label can be at or between nucleosides 18-24 and the other label at or between nucleosides 80-90; or one label can be at or between nucleosides 60-66, and the other label at or between nucleosides 80-90. This numbering system is from the *V. cholerae* glycine riboswitchwith an AP at nucleosides 1-90 and an EP at nucleosides 80-150.

For the THF riboswitch, one label can be at or between nucleosides 1-7 and the other label at or between 95-105; or one label can be at or between nucleosides 35-45 and the other label between nucleosides 85-100. This numbering is from the *E. siraeum* THF riboswitch with an AP at nucleosides 1-105 and an EP at nucleosides 85-150.

For the cyGG riboswitch, one label can be at or between nucleosides 1-18 and the other label at or between nucleosides 90-100. This numbering system is from the *Vibrio cholerae* tfoX cyGG riboswitch with an AP at nucleosides 1-100 and an EP ay nucleosides 80-130.

For the cobalamin B12 riboswitch, one label can be at or between nucleosides 148-170 and the other label at or between nucleosides 210-240. This numbering system is from the *E. coli* btuB B12 riboswitch with an AP at nucleosides 1-170 and an EP at nucleosides 150-280.

For immobilization, site-specific biotinylation achieves surface-immobilization via a biotin-streptavidin bridge to enable imaging of individual complexes over extended periods (ca. minutes to hours depending on the nature of the complex and buffer conditions). Biotinylation can be used to surface immobilize riboswitches within specialized microfluidic reaction chambers for both prism-based TIRF and zero-mode wave guide imaging. In one embodiment, the riboswitch is labeled at or near the 5' terminus. As an alternative strategy, the riboswitch is indirectly tethered within the imaging volume. For instance, the small subunit of the ribosome can be surface immobilized by directly biotinylating or epitope tagging one or more ribosomal proteins or through oligonucleotide hybridization to ribosomal RNA; the riboswitch can then be imaged as a consequence of its binding to the ribosome. Such strategies provide orthogonal vantage points from which to image dynamic ribosome-riboswitch interactions and the initiation process using the riboswitches of the invention.

The attachment of the riboswitch to the solid-phase substrate should employ the least dynamic part of the molecule, meaning via a structural element that is present in both of the mutually exclusive structures of the riboswitch. For example, residue P1 in pseudoknot forming riboswitches, and residues forming the loop L1/L2 interaction in purine riboswitches. Surface immobilization can also be achieved by incorporating physical extensions into non-essential portions of the riboswitch. For example, the 5' sequence of the riboswitch may be extended to include a sequence that enables the riboswitch to be tethered through its hybridization to a synthetic DNA oligonucleotide that is itself attached to solid support. Alternatively, an extension of one or more loop elements within the riboswitch element may be introduced in order to engineer a protein binding sequence (e.g. the RNA binding sequence for the U1A protein) into the riboswitch.

Modifications may include mutations to improve or alter functions of riboswitch or to increase or decrease the likelihood that the riboswitch will take on a certain conformation or exhibit movements that are on time scales suitable for imaging. Modifications can also include changing the anchoring method of the riboswitch to a substrate for imaging purposes.

Reaction conditions for imaging are known in the art. Further, cell-free, translation systems are available that perform with rates and fidelities comparable to those observed in vivo and operate over the range of divalent metal ion concentrations relevant to riboswtich studies (ca. 1-10 mM). Likewise, cell free transcription systems suitable for bulk fluorescence measurements and smFRET imaging are known in the art.

The fluorescence measurements and the imaging methods are known and described in the Definitions section. Moreover, the imaging method does not necessarily have to be limited to either single-molecule or total internal reflection based imaging methods as alternative embodiments of the invention are envisaged in which dynamics of the riboswitch regulatory domain could be assessed using alternative methods such as bulk fluorescence imaging methods and/or indirect readout methods, where a downstream reporter is used to assess riboswitch dynamics.

The studies described here show that ligand binding can lead to changes in the propensity for sequestration of the regulatory domain thus leading to down regulation of translation and that ligand binding may also lead to the inverse effect, in which case upregulation of translation may occur. Overall, the data implicate the value directly assessing the relationship between ligand binding to an aptamer domain and changes in accessibility of the expression platform domain. The reagents and methods described herein provide a general means of screening for agents that impact this dynamic regulatory circuit.

For smFRET studies of the SAM-II riboswitch (PDB code: 2QWY), at least two locations can be labeled. For a first label, any position within or near the SD sequence (residues about 47 to about 53) may be used. For a second label, a position in loop region (residues about 10 to about 22) is useful, including those residues that are extruded and accessible to solvent. (for example A14).

The unliganded SAM-II riboswitch is highly dynamic in nature, where its conserved stem-loop element becomes engaged in a pseudoknot fold through base-pairing with nucleosides in the single-stranded 3'-overhang. The pseudoknot structure is highly transient in the absence of its ligand, SAM, and becomes conformationally restrained upon ligand recognition. The smFRET experiments revealed the underlying dynamics of pseudoknot sampling in the free state to be on the order of hundreds of milliseconds. To achieve a highly reliable smFRET data set, the modification pattern was chosen in a way to immobilize the riboswitch at the least dynamic segment, namely the hairpin stem which is preorganized even in the absence of $Mg^{2+}$. Importantly, this immobilization did not compromise the pseudoknot region of the molecule that was expected to be dynamic. Attaching fluorophores at the Shine-Dalgarno sequence and the hairpin loop were therefore ideally positioned to directly sense the regulatory interaction, namely pseudoknot formation (FIG. 5).

3. Methods

Riboswitches regulate gene expression by turning on or turning off transcription and/or translation. For example, by examining the effects of a test compound on the conformation of a riboswitch that controls the expression of a gene that leads to a cytotoxic effect in bacteria, one can identify potential antibiotics for treating bacterial infections. Alternatively, test compounds can be screened for their capacity to prevent the cognate ligand from performing its normal functions (e.g., by competitively blocking ligand binding) and thereby preventing or reducing ligand-induced control of gene expression.

As part of the invention, thus, one aspect of the invention is directed to methods to detect structural changes in the expression platform domain of a riboswitch by determining the FRET states of a riboswitch of the invention for a time and under varying conditions. Varing the conditions includes, but is not limited to, the presence or absence of a ligand for the riboswitch, changing concentrations of that ligand, the presence or absence of a cofactor that interacts with the riboswitch, changing concentrations of that cofactor, presence or absence of transcription components, changing concentrations of those transcription components, the presence or absence of translation initiation components, and changing concentration of those translation components.

In addition, these methods can be conducted to search for modulators of riboswitch activity. In this case, a candidate modulater is added to the reaction, the FRET states of the riboswitch are determined and the regulatory consequences ascertained, i.e., whether transcription is turned on/off or translation is turned on/off based on the regulatory activity of the particular riboswitch being assayed. Hence, changes in the FRET distributions under a specific set of conditions indicates the relationship between aptamer domain binding and sequestration or liberation of the expression platform domain.

Any of the riboswitches of the invention can be used in these methods and FRET states are detected by bulk fluorescence detection or by smFRET imaging techniques as described hereinabove.

In another embodiment, the invention provides methods to identify a compound that interferes with riboswitch function by (a) surface-immobilizing a riboswitch of the invention, wherein there is a FRET pair present that is sensitive to transitioning between a low FRET state and a high FRET state under transcription and/or translation competent conditions; (b) adding a test compound to the riboswitch; and (c) monitoring or detecting changes in FRET states using smFRET imaging techniques to identify a test compound capable of (i) stabilizing the riboswitch in a low FRET state, an intermediate FRET state or in a high FRET state, (ii) changing the riboswitch's distribution among low, intermediate and high FRET states, (iii) changing the riboswitch's rate of transition among low, intermediate and high FRET states, or (iv) abolishing FRET.

In certain embodiments, the FRET pair is formed by a fluorophore on the expression platform domain and a fluorophore on the aptamer domain. In other embodiments, the FRET pair is formed by a fluorophore on the expression platform domain and a fluorophore on the ligand of the said riboswitch. In another embodiment, the FRET pair is formed by a fluorophore on the expression platform domain and a fluorophore on the 30S subunit of a ribosome. In any event, a test compound is identified as a candidate antibiotic when it causes the riboswitch to adopt a FRET state which correlates with cytotoxic activity to bacteria.

The present description is further illustrated by the following examples, which should not be construed as limiting in any way. The contents of all cited references (including literature references, issued patents, published patent applications as cited throughout this application) are hereby expressly incorporated by reference.

EXAMPLE 1

General Methods and RNA Preparation

1. Solid-Phase Synthesis of Oligoribonucleotides

All oligonucleotides were synthesized on Pharmacia instruments (Gene Assembler Plus) following DNA/RNA standard methods.

Detritylation (2.0 min): dichloroacetic acid/1,2-dichloroethane (4/96); coupling (3.0 min): phosphoramidites/acetonitrile (0.1 M×120 μL) were activated by benzylthiotetrazole/acetonitrile (0.3 M×360 μL); capping (3×0.4 min): A: $Ac_2O$/sym-collidine/acetonitrile (20/30/50), B: 4-(dimethylamino)pyridine/acetonitrile (0.5 M), A/B=1/1; oxidation (1.0 min): $I_2$ (10 mM) in acetonitrile/sym-collidine/$H_2O$ (10/1/5). For 5-aminoallyl-uridine sequences, mild capping solutions were used: A: 0.2 M phenoxyacetic anhydride in THF, B: 0.2 M N-methylimidazole and 0.2 M sym-collidine in THF. Acetonitrile, solutions of amidites and tetrazole were dried over activated molecular sieves overnight.

2'-O-TOM standard nucleoside phosphoramidites were obtained from GlenResearch or ChemGenes. 5'-Biotin phosphoramidite was purchased from GlenResearch. 5-Aminoallyl-uridine phosphoramidite was purchased from Berry&Associates. $N^4$-acetyl-2'-O-(tert-butyldimethylsilyl)-5'-O-(4,4'-dimethoxytrityl)-5-fluorocytidine phosphoramidite was synthesized according to Puffer 2009. All solid supports for RNA synthesis were purchased from GE Healthcare (Custom Primer Supports: riboC Ac 80, riboA 80, riboG 80, riboU 80).

2. Deprotection of Oligonucleotides

RNA oligonucleotides were deprotected by using $CH_3NH_2$ in EtOH (8 M, 0.65 mL) and $CH_3NH_2$ in $H_2O$ (40%, 0.65 mL) at room temperature for 6-8 h. After complete evaporation of the solution, the 2'-O-TOM protecting groups were removed by treatment with tetrabutylammonium fluoride trihydrate (TBAF.3$H_2O$) in THF (1 M, 1.0-1.5 mL) for at least 14 h at 37° C. The reaction was quenched by addition of triethylammonium acetate (TEAA) (1 M, pH 7.0, 1.0-1.5 mL). The volume of the solution was reduced to 0.8 mL and the solution was loaded on a GE Healthcare HiPrep 26/10 desalting column (2.6×10 cm; Sephadex G25). The crude RNA was eluted with $H_2O$, evaporated to dryness and dissolved in 1.0 mL of nanopure water.

3. Analysis, Purification, and Mass Spectrometry of Oligoribonucleotides

Analysis of crude oligonucleotides after deprotection was performed by anion-exchange chromatography on a Dionex DNAPac100 column (4×250 mm) at 80° C. (60° C. for the 5-aminoallyl-uridine RNA variants). Flow rate: 1 mL/min; eluant A: 25 mM Tris-HCl pH 8.0, 6 M urea; eluant B: 25 mM Tris-HCl pH 8.0, 0.5 M $NaClO_4$, 6 M urea; gradient: 0-60% B in A within 45 min; UV-detection at 260 nm.

Crude RNA products (trityl-off) were purified on a semi-preparative Dionex DNAPac100 column (9×250 mm) at 80° C. (60° C. for the 5-aminoallyl-uridine sequences). Flow rate: 2 mL/min; gradient: 412-22% B in A within 20 min. Fractions containing oligonucleotide were loaded on a C18 SepPak cartridge (Waters/Millipore), washed with 0.1 M $(Et_3NH)^+$ $HCO_3^-$ and $H_2O$, eluted with $H_2O$/$CH_3CN$ 1/1 and lyophilized to dryness.

The purified oligonucleotides were characterized by mass spectrometry on a Finnigan LCQ Advantage MAX ion trap instrumentation connected to an Amersham Ettan micro LC system (negative-ion mode with a potential of −4 kV applied to the spray needle). LC: Sample (200 pmol of oligonucleotide dissolved in 30 μL of 20 mM EDTA solution; average injection volume: 30 μL); column (Xterra® MS, C18 2.5 μm; 1.0×50 mm) at 21° C.; flow rate: 100 μL/min; eluant A: 8.6 mM TEA, 100 mM 1,1,1,3,3,3-hexafluoro-2-propanol in $H_2O$ (pH 8.0); eluant B: methanol; gradient: 0-100% B in A within 30 min; UV detection at 254 nm.

EXAMPLE 2

Bulk Fret Detection of Pseudoknot Formation

NMR studies (Haller 2011) provided structural insights for designing fluorescently-labeled SAM-II riboswitch constructs for following pseudoknot formation using a FRET-based approach. Through such experiments, the formation of P2a helix, reflecting the sequestration of the SD sequence, was followed.

1. Preparation of Cy3/Cy5 Labeled Oligoribonucleotides

Cy3 and Cy5 NHS esters were purchased from GE Healthcare. DMSO was dried over activated molecular sieves.

Labeling was performed according to Solomatin 2009, with slight modifications as described below: Dye-NHS ester (1 mg; ~1300 nmol) was dissolved in anhydrous DMSO (500 μL). Lyophilized RNA (20 nmol) containing the 5-aminoallyluridine modification was dissolved in labeling buffer (20 μL; 500 mM phosphate buffer pH=8.0) and nanopure water was added to reach a fraction of 55% (v/v) (122 μL) of the intended final reaction volume (222 μL) with a final concentration of $c_{RNA}$ of 90 μM. The corresponding volume of the dye-NHS ester solution (45% (v/v)) (100 μL) was added to the RNA solution (to reach a concentration of $c_{Dye}$=1.17 mM in the final reaction volume). The reaction mixture was gently tumbled on a shaker overnight at room temperature in the dark.

Products were purified by precipitation with 2.5 equivalents of reaction volumes containing 0.3 mM sodium acetate in 80% ethanol for 20 min at −20° C. and centrifuged for 20 min at 4° C. at 13000 rpm to remove the excess of unreacted and hydrolyzed dye. The pellets were washed with 70% cold ethanol and dried under air and high vacuum. The dried pellets were resuspended in water and purified by anion-exchange chromatography on a Dionex DNAPac100 column (9×250 mm) at 60° C. Flow rate: 2 mL/min; gradient: Δ12-22% B in A within 20 min; UV-detection at a wavelength λ, of 260 nm (RNA), 548 nm (Cy3), and 646 nm (Cy5). Fractions containing labeled oligonucleotide were loaded on a C18 SepPak cartridge (Waters/Millipore), washed with 0.1 M $(Et_3NH)^+HCO_3^-$ and $H_2O$, eluted with $H_2O/CH_3CN$ 1/1 and lyophilized to dryness.

2. Enzymatic Ligation

Enzymatic ligations were performed along the lines described in Lang 2008. The use of T4 DNA ligase requires a double-stranded ternary substrate formed by a 5'-phosphorylated RNA donor, a single stranded RNA acceptor with a free 3'-OH group, and a splint oligonucleotide. Hence, the following fragments were used:

33 nt RNA acceptor strand:

```
                                          (SEQ ID NO. 1)
5'-UCG CGC UGA UUU AAC CGU AUU GCA AGC GCG UGA-3';
``` p19p nt RNA donor strand for the 52 nt RNA sequence:

```
                                          (SEQ ID NO. 2)
         5'-p UAA AUG UAG CUA AAA AGG G p-3';
``` and
Splint 30 nt DNA:

```
                                          (SEQ ID NO. 3)
      5'-TTT TAG CTA CAT TTA TCA CGC GCT TGC AAT-3'.
```

To optimize ligation conditions, ligation reactions were first performed on an analytical scale (0.2 to 1 nmol) with different lengths of DNA splint before proceeding on preparative scale (20 nmol). T4 DNA ligase was purchased from Fermentas (5 U/µL). Optimal ligation conditions were 10 µM for each RNA fragment, a 30 nt DNA splint, and final ligase concentration of 0.5 U/µL in a final volume of 2 ml with reaction for 12 h at 37° C.

Analysis of the ligation reaction and purification of the ligation products were performed by anion exchange chromatography. LC ESI MS was used for characterization of the HPLC-purified RNA. The yield of the SAM-II riboswitch was higher than 40% after purification by anion exchange chromatography (52 nt: 10.4 nmol, $OD^{260}$~6.1).

3. Steady-State Fluorescence Spectroscopy

All experiments were measured on a Cary Eclipse spectrometer (Varian, Palo Alto, USA) equipped with a peltier block, a magnetic stirring device, and a RX2000 stopped-flow apparatus (Applied Photophysics Ltd., Leatherhead, UK).

4. Results

Figure 1:
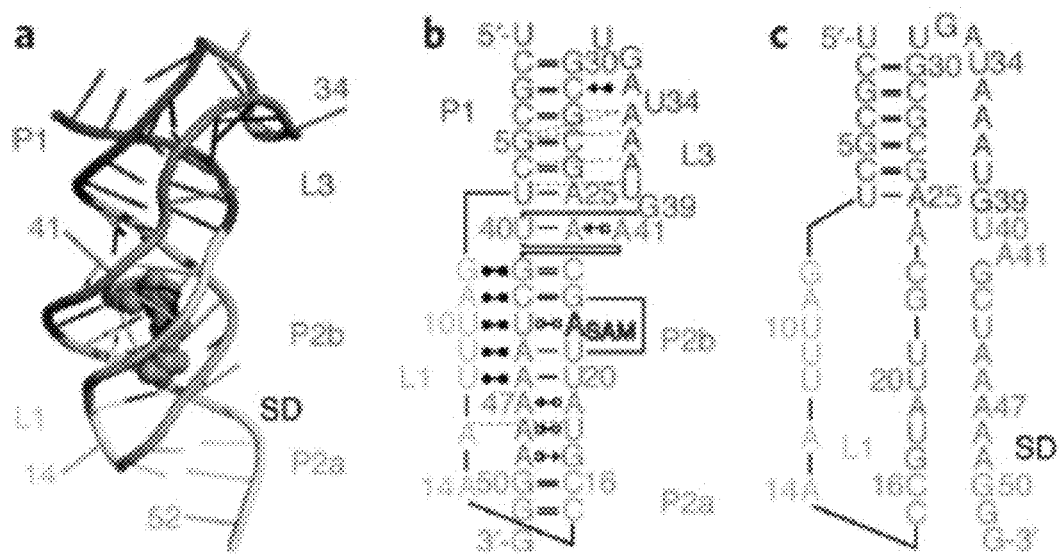
FIG. 1 depicts the metX SAM-II RNA (a) bound to S-adenosylmethionine (SAM) (Gilbert 2008) as a cartoon and (b) showing secondary/tertiary structure interactions in Leontis-Westhof nomenclature (Lescoute 2006). (c) A minimal secondary structure model of the unliganded SAM-II RNA is shown. SD, Shine-Dalgarno sequence.

Based on the reported structure of the SAM-II riboswitch (Gilbert 2008), an acceptor (Cy5) fluorophore was attached to the non-conserved nucleoside at position 14, and a donor (Cy3) fluorophore at the unpaired terminal residue at position 52 (FIG. 1a).

Figure 2:
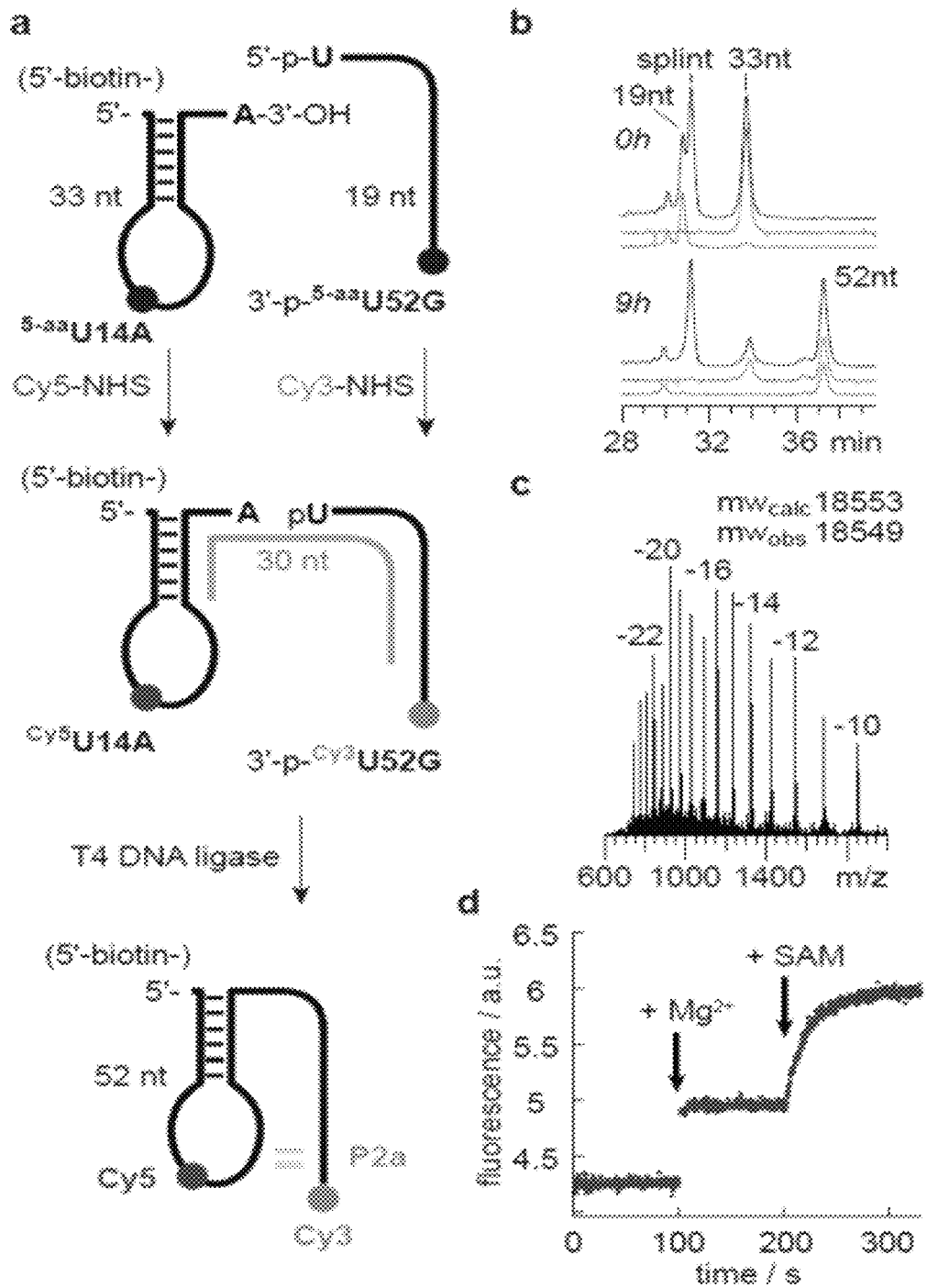
FIG. 2 illustrates the construction of a Cy3/Cy5-labeled SAM-II construct sensitive to pseudoknot formation. (a) The strategy for synthesis, labeling and enzymatic ligation is shown, with the chemical structures of fluorophores and linkers provided in FIG. 3. (b) Anion-exchange (AE) HPLC trace of enzymatic ligation using T4 DNA ligase and a DNA splint at the start (0 h) and after completion (9 h). The product (retention time=37.3 min) was purified by AE-HPLC. (c)

Riboswitch variants possessing this labeling arrangement were constructed by synthesizing two fragments of 33 and 19 nt in length, each carrying a single 5-aminoallyl uridine nucleoside at the selected positions (FIG. 2, FIG. 3). The individual strands were coupled with their respective fluorophores by reaction with N-hydroxysuccinimide-activated forms of Cy3 and Cy5, respectively. The separated fluorescently labeled strands were purified by anion exchange chromatography, and enzymatically ligated (Lang 2008) using T4 DNA ligase and a 30 nt DNA splint (75% yield) (FIG. 2b). After HPLC purification, LC-ESI mass spectrometry confirmed that the pure ligated product had the expected molecular weight (FIG. 2c).

Upon addition of 10 equivalents of SAM to the Cy3/Cy5-labeled riboswitch, fluorescence emission from the acceptor fluorophore, achieved via FRET (FIG. 2d), was shown to dramatically increase in intensity consistent with its transition from a relatively open fold to a pseudoknot like structure. The rate of increase followed single exponential behavior, where the observed rate was $1.19 \pm 0.06 \times 10^{-2}$ $s^{-1}$ (6 equivalents of SAM).

EXAMPLE 3 smFRET for Sensing Pseudoknot Formation

To reveal the underlying dynamics of SAM-II pseudoknot formation, single-molecule FRET (smFRET) (Aleman 2008; Lemay 2006; Brenner 2010) investigations were performed using the same labeling strategy as in Example 2 (i.e., $A14^{Cy3}U$ and $G52^{Cy5}U$). To enable surface immobilization of the SAM-II riboswitch within a passivated microfluidic device and extended observation periods, a 5'-biotin moiety was included in the design (FIG. 2, FIG. 3).

1. Acquisition of smFRET Data smFRET data were acquired using a prism-based total internal reflection (TIR) microscope, where the biotinylated SAM-II riboswitch was surface immobilized within PEG-passivated, strepatividin-coated quartz microfluidic devices (Munro 2007). The Cy3 fluorophore was directly illuminated under 1.5 kW/cm² intensity at 532 nm (Laser Quantum). Photons emitted from both Cy3 and Cy5 were collected using a 1.2 NA 60× Plan-APO water-immersion objective (Nikon), where optical treatments were used to spatially separate Cy3 and Cy5 frequencies onto two, synchronized EMCCD devices (Evolve 512, Photometrics). Fluorescence data were acquired using MetaMorph acquisition software (Universal Imaging Corporation) at a rate of 66.7 frames per second (15 ms integration). Fluorescence trajectories were selected from the movie files for analysis using automated image analysis software coded in Matlab (The MathWorks). Fluorescence trajectories were selected based on the following criteria: a single catastrophic photobleaching event, at least 6:1 signal-to-background noise ratio (SNR) calculated from the total fluorescence intensity, and a FRET lifetime of at least 30 frames (450 ms) in any FRET state ≥0.15. smFRET trajectories were calculated from the acquired fluorescence data using the formula $FRET = I_{Cy5}/(I_{Cy3} + I_{Cy5})$, where $I_{Cy3}$ and $I_{Cy5}$ represent the Cy3 and Cy5 fluorescence intensities, respectively. Equilibrium smFRET experiments were performed in 50 mM KMOPS, 100 mM KCl, pH 7.5 buffer in the presence of an optimized oxygen scavenging and triplet state quenching cocktail in the presence of an oxygen scavenging environment (1 unit protocatchuate-3,4-dioxygenase, 2 mM protocatechuic acid; 1 mM Trolox, 1 mM cyclooctatetraene, 1 mM nitrobenzyl-alcohol) (Dave 2009). Concentrations of $MgCl_2$ and SAM were as specified in the figure captions.

FRET state occupancies and transition rates were estimated by idealization to a two-state Markov chain model (0.2 FRET; 0.8 FRET) using the segmental k-means algorithm implemented in QuB. (Qin 2004).

2. Results

As previously described, the emission intensities of both Cy3 and Cy5 fluorophores were tracked simultaneously for individual surface-immobilized molecules using a wide-field, prism-based total internal reflection configuration, with a single-frequency light source (532 nm) (Munro 2007). The measurements obtained were divided into three subgroups: 1) without $Mg^{2+}$ ions, 2) with $Mg^{2+}$ ions (2 mM), and 3) the with $Mg^{2+}$ ions (2 mM) and saturating concentrations of SAM (10 µM). Under conditions that support extended stabilization of the Cy3 and Cy5 fluorophores, high signal-to-noise (>5:1) time-dependent FRET information was obtained from individual SAM-II riboswitch molecules (>1000 molecules) for each imaging condition at an imaging rate of 66 frames per second (15 ms integration time). Under such conditions, the average lifetime of FRET observed, <τFRET>, was ~3.5 seconds, limited predominantly by Cy5 fluorophore photobleaching. The dynamic behaviors of individual molecules were assessed using hidden Markov modeling (HMM) procedures, and ensemble information was obtained by assembling single-molecule FRET trajectories into population FRET histograms. (Munro 2007)

In the absence of $Mg^{2+}$ and SAM, a dominant, low-FRET (0.30) configuration of the SAM-II riboswitch was observed. This FRET value was consistent with a relatively open conformation of the riboswitch platform, wherein the dyes are separated by approximately 65 Å (FIG. 4a, upper left panel). Very low occupancy of a high-FRET (approximately 0.85) configuration was also observed, consistent with an interdye distance <20 Å (FIG. 4a, upper right panel). Inspection of individual FRET trajectories revealed that such conformations resulted from frequent (approximately 5 $s^{-1}$), transient (approximately 30 ms lifetime) high-FRET state excursions from the predominant, low-FRET configuration (FIG. 4a, lower panel). These data suggested that the SAM-II riboswitch can intrinsically achieve a pseudoknot-like fold even in the absence of $Mg^{2+}$ or SAM ligands, but that the folded riboswitch was highly unstable in nature.

In the presence of $Mg^{2+}$, the high-FRET state was significantly stabilized (approximately 10-fold). Such stabilization resulted in an equal distribution of open (low-FRET) and compacted (high-FRET) riboswitch conformations (FIG. 4b, upper panels). The absolute value of the low-FRET state was observed to increase by 0.08 in the presence of $Mg^{2+}$. This observation suggests that $Mg^{2+}$ binding tends to slightly compact or rigidify the apo-riboswitch fold. Through the inspection of individual FRET trajectories, shifts in FRET distribution could be attributed principally to three effects: 1) a subpopulation (~50%) that shifted from the dynamic, low-FRET configuration observed in the absence of $Mg^{2+}$ to the slightly compacted, increased FRET configuration (0.38), which displayed greatly reduced dynamics (approximately 2 second lifetime); 2) a second sub-population (~30%) that exhibited rapid dynamics between low—(0.38) and high—(0.85) FRET states, where the high-FRET state lifetime was increased 10-fold; and 3) a sub-population (~10%) that resided in a relatively stable (about 2 second lifetime), high-FRET (0.85) state. Remarkably, a slow exchange between sub-populations was observed in approximately 1-5% of the imaged molecules (FIG. 4b, lower panel).

In the presence of $Mg^{2+}$ and SAM a dominant high-FRET state was observed consistent with ligand-induced stabilization of a compacted pseudoknot conformation (FIG. 4c, upper panels). An analysis of individual FRET trajectories revealed that such effects resulted predominantly from about a 10-fold stabilization of the high-FRET state. Under such conditions, the average dwell time in the high-FRET state was approximately one second, where only rare, transient excursions to lower-FRET states were observed (FIG. 4c, lower panels).

3. Discussion

A model describing the SAM-II riboswitch folding pathway in global terms is illustrated by a cartoon in FIG. 5. In the absence of ligand and in the absence of $Mg^{2+}$ ions, the riboswitch domain adopts a stem-loop conformation with a flexible unpaired oligonucleotide stretch at the 3'-side, which contains the Shine-Dalgarno sequence (I). Rare excursions to closed conformations are transient in nature (ca. <50 ms) such that the system rapidly returns to unfolded configurations. However, at physiological conditions with $Mg^{2+}$ in the low millimolar concentration range, this closed conformation becomes significantly populated, where pseudoknot-like folds, competent for SAM binding persist for approximately 100-500 milliseconds (III). As observed in individual smFRET trajectories, unfolded riboswitch conformations can persist for several seconds (II); the system can then enter a rapid dynamics regime, where fluctuations occur between hairpin (II) and pseudoknot-like states (III).

Magnesium ions tend to compact the apo-riboswitch structure, in particular the P1/L3 interactions. This suggest that $Mg^{2+}$ promotes preorganizing and orientating of the adjacent strands, ultimately allowing the consecutive base triples U40/A24/A41, G8/G42/C23, and A9/C43/G22 to form. In turn, such conformations provide the platform for intercalation of the SAM nucleobase.

The transient, pseudoknot-like fold of the free riboswitch (III) observed in the presence of $Mg^{2+}$ likely resembles the global fold of SAM-bound structure (IV). The kinetics of SAM binding suggest that achieving state III precedes or immediately follows initial ligand/RNA contacts. Structures in which only stem P1 (I) or P1/L3 interactions are present (II) likely lack the potential for high-affinity SAM binding. Based on the architecture of the fully folded SAM-II riboswitch (Gilbert 2008) and in line with a recent molecular dynamics simulation (Kelley 2010), SAM could approach and enter its binding site without global conformational changes (see FIG. 6). Taken together, the data suggest that SAM likely binds and stabilizes the pseudoknot-like conformations (III). The triple-stranded arrangement of the binding pocket, where contacts between P2b and L1 begin to form, remains conformationally mobile in the absence of ligand. SAM binding and intercalation between U21 and G22 stabilizes a more compact riboswitch fold in which the purine-rich, A46-A49 sequence achieves a tight hydrogen-bond network with the major groove of P2 helix (IV). The culmination of this process is the formation of the P2a helix.

The present investigation on the SAM-II riboswitch contributes to further understand the dynamics of RNA and its importance for ligand recognition in biomolecular regulation processes. The single-molecule experiments document the fluctuation of this short riboswitch between the two ensemble states of a hairpin (II) and a loose pseudoknot (III), the latter being structurally close to the final SAM-bound RNA complex (FIG. 5). Pseudoknot III stands for the selected conformation. In this view, the propensity to the SAM-II riboswitch to dynamically sample both unfolded and pseudoknot-like conformations plays a role in the ligand recognition process and the regulatory switch mechanism. In the context of the intact mRNA, such features render the system responsive to both the cellular milieu and ligand concentration to appropriately sequester the Shine-Dalgarno sequence and down regulate translation.

EXAMPLE 4

Purine Riboswitch

The purine riboswitch forms a three-way, helical junction closed by the "regulatory" P1 helix, which comprises the interface between aptamer and expression platform The adenosine deaminase (add) riboswitch from *Vibrio vulnificus* is modified for FRET studies by placing an immobilization moiety into the non-conserved residues within the L2 loop. The donor (Cy3) and acceptor (Cy5) fluorophores are introduced into the opposite strands of the P1 helix (FIG. 7A). Labeled riboswitch constructs are prepared by chemical synthesis of half-molecules with site-specific amino modifications by standard RNA solid-phase synthesis generally as described in Example 1 and 2.

The construct for the investigation of translation initiation is the full-length add riboswitch having both the aptamer and expression platform domains, and optionally including the SD sequence and the first 7-10 codons of the ORF sequence (FIG. 7B). This full-length add riboswitch is interrogated using bulk fluorescence and smFRET without the ribosomal initiation machinery to determine intrinsic dynamic properties and to investigate translation initiation processes.

Further, modifications of this riboswitch can be used with a small ribosomal subunit that is site-specifically labeled through ribosomal proteins located proximal to the anti-SD sequence as can be determined from crystallographic and functional data (FIG. 8B). Such labels can be introduced by the method of Yin 2006. In this case the riboswitch contains a a single donor (Cy3) fluorophore and the 30S subunit contains a with a single acceptor (Cy5) fluorophore.

Bulk fluorescence and smFRET measurements are conducted as described in Examples 2 and 3.

EXAMPLE 5

Ligand Labeling Studies

A single acceptor fluorophore is introduced into the SAM ligand and used to perform 3-color FRET experiments. Several SAM derivatives are shown in FIG. 9 and these derivatives, with aliphatic extensions (such as a propyl group instead of the S-methyl group), bind the SAM-II riboswitch with nearly wild-type affinity (FIG. 9).

Fluorophore-labeled SAM and the SAM-II riboswitch with a donor fluorophore at position 52 (constructed as described in Example 2) are used in bulk fluorescence and smFRET measurements as described herein to examine the FRET states under various conditions.

In one example, the relationship between Cy2-labeled SAM binding to a Cy3- and Cy5-labeled SAMII riboswitch is determined by directly exciting the surface-immobilized SAMII riboswitch to monitor dynamics in the presence of Cy2-labeled SAM ligand in excess concentration in solution while simultaneously illuminating the sample with a single-frequency 473 nm laser. Ligand binding is determined by the colocalization of Cy2-SAM ligand to the region of the surface containing the FRET-labeled riboswitch. Alternatively, SAM ligand localization to the FRET labeled riboswitch is determined using FRET from Cy2 to the Cy3 fluorophore upon its interaction with the riboswitch. FRET configurations are also envisaged in which only direct Cy3 illumination is required. For instance, the SAM ligand can be labeled with either a Cy5.5 or Cy7 fluorophore, where binding to the riboswitch and its specific conformation is revealed by energy transfer from the fluorophores on the riboswitch to the fluorophore on the SAM ligand.

REFERENCES

Alemán et al. (2008) *Curr. Opin. Chem. Biol.* 12, 647-654.
Baird et al. (2010b) *RNA* 16, 598-609.
Blouin et al. (2009) *Chembiochem* 10, 400-416.
Brenner et al. (2010) *Biochemistry* 49, 1596-1605.
Clegg et al., (1992) *Biochemistry* 31, 4846-4856.
Corbino et al. (2005) *Genome Biol.* 6, R70.
Dave et al. (2009) *Biophys. J.* 96, 2371-2381.
Edwards et al. (2010) *RNA* on-line.
Garst et al. (2009) *Biochim. Biophys. Acta* 1789, 584-591.
Geen (1991) *J. Magn. Reson.* 93, 93-141.
Gilbert et al. (2008) *Nat. Struct. Mol. Biol.* 15, 177-182.
Haller et al. (2011) *Nat. Chem. Biol.* 7, 393-400, Epub May 1, 2011.
Kelley et al. (2010) *Nucl. Acids Res.* 38, 1392-1400.
Lang et al. (2008) *Nat. Protoc.* 3, 1457-1466.
Lang et al. (2007) *Nucl. Acids Res.* 35, 5370-5378.
Lemay et al. (2006) *Chem. Biol.* 13, 857-868.
Lescoute et al. (2006) *Nucl. Acids Res.* 34, 6587-6604.
Lu et al. (2010) *J. Mol. Biol.* 404, 803-818.
Montange et al. (2008) *Annu. Rev. Biophys.* 37, 117-133.
Munro et al. (2007) *Mol. Cell.* 25, 505-517.
Poiata et al. (2009) *RNA* 15, 2046-2056.
Puffer et al. (2009) *Nucleic Acids Res.* 37, 7728-7740.
Qin et al. (2004) *Biophys. J.* 87, 1657-1671.
Roth et al. (2009) *Annu. Rev. Biochem.* 78, 305-334.
Solomatin et al. (2009) *Methods Enzymol.* 469, 47-68.
Stoddard et al. (2010) *Structure* 18, 787-797.
Wang et al. (2008) *Biochem. Cell Biol.* 86, 157-168.
Yin et al. (2006) *Nat. Protoc.* 1, 280-5.

We claim:

1. An isolated riboswitch which comprises an aptamer domain, an expression platform domain, and at least one fluorophore attached to said expression platform domain of the riboswitch, which fluorophore serves as the first fluorophore of a FRET pair of fluorophores having FRET states capable of distinguishing changes in regulatory interactions controlled by said expression platform domain.

2. The riboswitch of claim 1 which further comprises a ribosome binding site.

3. The riboswitch of claim 1 or 2, wherein the second fluorophore of said FRET pair is attached to said riboswitch, is attached to a ligand or is attached to a 30S subunit of a ribosome.

4. The riboswitch of claim 3, wherein the fluorophores of said FRET pair are acceptor-donor fluorophores or donor-quencher fluorophores.

5. An isolated riboswitch which comprises an aptamer domain, an expression platform domain, and a FRET pair of fluorophores which have FRET states capable of distinguishing changes in regulatory interactions controlled by said expression platform domain, wherein at least one fluorophores of said FRET pair is attached to the expression platform domain.

6. The riboswitch of claim 5, wherein said regulatory interactions are detected as structural changes in said expression domain in the presence and absence of a ligand for said riboswitch.

7. The riboswitch of claim 5, wherein one fluorophore of said pair is on the expression platform domain and the other fluorophore of said pair is on the aptamer domain.

8. The riboswitch of claim 5 which further comprises a ribosome binding site.

9. The riboswitch of claim 5, wherein the fluorophores of said FRET pair are acceptor-donor fluorophores or donor-quencher fluorophores.

10. The riboswitch of claim 1 or 5, wherein said riboswitch is selected from the group consisting of an adenine riboswitch, a guanine riboswitch, a 2'-deoxyguanosine riboswitch, a preQ1 I-II riboswitch, a SAH riboswitch, a SAM I-IV riboswitch, a cobalamin B12 riboswitch, a fluorine riboswitch, an FMN riboswitch, a TPP riboswitch, a lysine riboswitch, a glycine riboswitch, a THF riboswitch, a glutamine riboswitch, a glmS riboswitch, a molybdenum cofactor (MoCo) riboswitch, and a cyclic di-GMP riboswitch.

11. The riboswitch of claim 1 or 5, wherein said riboswitch is an S-adenosylmethionine (SAM) type riboswitch.

12. The riboswitch of claim, 11 wherein said riboswitch is a SAM-type II riboswitch.

13. The riboswitch of claim 12 wherein said fluorophores are at nucleoside positions 14 and 52 of said riboswitch.

14. The riboswitch of claim 1 or 5, which further comprises an immobilization moiety.

15. The riboswitch of claim 14 wherein said immobilization moiety is at the 5' end of said riboswitch.

16. A method to detect structural changes in the expression platform domain of a riboswitch which comprises determining the FRET states of a riboswitch of claim 1 or 5 for a time and under varying conditions.

17. The method of claim 16, wherein said varying conditions are selected from the group consisting of presence or absence of a ligand for said riboswitch, changing concentrations of said ligand, presence or absence of a cofactor that interacts with said riboswitch, changing concentrations of said cofactor, presence or absence of transcription components, changing concentrations of said transcription components, presence or absence of translation initiation components, and changing concentration of said translation components.

18. The method of claim 16 which further comprises adding a modulator of riboswitch activity and determining the FRET states of said a riboswitch.

19. The method of claim 16, wherein changes in FRET state indicates the relationship between aptamer domain binding and sequestration or liberation of the expression platform domain.

20. The method of claim 16, wherein said FRET states are detected by bulk fluorescence detection or by smFRET imaging techniques.

21. A method to identify a compound that interferes with riboswitch function which comprises
   (a) surface-immobilizing a riboswitch of claim 1 or 5, wherein a FRET pair is present and sensitive to transitioning between a low FRET state and a high FRET state under transcription and/or translation competent conditions;

(b) adding a test compound to said riboswitch; and
(c) monitoring or detecting changes in FRET states using smFRET imaging techniques to identify a test compound capable of
   (i) stabilizing said riboswitch in a low FRET state, an intermediate FRET state or in a high FRET state,
   (ii) changing said riboswitch's distribution among low, intermediate and high FRET states,
   (iii) changing the riboswitch's rate of transition among low, intermediate and high FRET states, or
   (iv) abolishing FRET.

22. The method of claim 21, wherein said FRET pair is formed by a first fluorophore on said expression platform domain and a second fluorophore on said aptamer domain.

23. The method of claim 21, wherein said FRET pair is formed by a first fluorophore on said expression platform domain and a second fluorophore on a ligand of said riboswitch.

24. The method of claim 21, wherein said FRET pair is formed by a first fluorophore on said expression platform domain and a second fluorophore on a 30S subunit of a ribosome.

25. The method of claim 21, wherein said compound is identified as a candidate antibiotic when said test compound causes said riboswitch to adopt a FRET state which correlates with cytotoxicity to bacteria.

26. The method of claim 21, wherein said FRET pair consists of a donor-acceptor fluorophore pair or a donor-quencher fluorophore pair.

* * * * *

SEQUENCE LISTING

<160> NUMBER OF SEQ ID NOS: 3

<210> SEQ ID NO 1
<211> LENGTH: 33
<212> TYPE: RNA
<213> ORGANISM: Artificial Sequence
<220> FEATURE:
<223> OTHER INFORMATION: RNA acceptor strand

<400> SEQUENCE: 1
ucgcgcugau uuaaccguau ugcaagcgcg uga                33

```
<210> SEQ ID NO 2
<211> LENGTH: 19
<212> TYPE: RNA
<213> ORGANISM: Artificial Sequence
<220> FEATURE:
<223> OTHER INFORMATION: RNA donor strand

<400> SEQUENCE: 2
uaaauguagc uaaaaaggg                                               19

<210> SEQ ID NO 3
<211> LENGTH: 30
<212> TYPE: DNA
<213> ORGANISM: Artificial Sequence
<220> FEATURE:
<223> OTHER INFORMATION: Splint DNA

<400> SEQUENCE: 3
ttttagctac atttatcacg cgcttgcaat                                   30
```